United States Patent
Kim et al.

(10) Patent No.: US 9,375,483 B2
(45) Date of Patent: Jun. 28, 2016

(54) STABLE LIQUID PHARMACEUTICAL COMPOSITION CONTAINING PIROXICAM OR ITS PHARMACEUTICALLY ACCEPTABLE SALT AND HYALURONIC ACID OR ITS PHARMACEUTICALLY ACCEPTABLE SALT AND THE MANUFACTURING METHOD THEREOF

(71) Applicant: DONG-A ST CO., LTD., Seoul (KR)

(72) Inventors: Soon-Hoe Kim, Suwon-si (KR); Mi-Won Son, Yongin-si (KR); Sun-Woo Jang, Seoul (KR); Myung-Joo Kang, Yongin-si (KR); Kyung-Wan Ma, Yongin-si (KR)

(73) Assignee: DONG-A ST CO., LTD., Seoul (KR)

( * ) Notice: Subject to any disclaimer, the term of this patent is extended or adjusted under 35 U.S.C. 154(b) by 0 days.

(21) Appl. No.: 14/384,084

(22) PCT Filed: Mar. 7, 2013

(86) PCT No.: PCT/KR2013/001856
§ 371 (c)(1),
(2) Date: Sep. 9, 2014

(87) PCT Pub. No.: WO2013/133647
PCT Pub. Date: Sep. 12, 2013

(65) Prior Publication Data
US 2015/0051168 A1 Feb. 19, 2015

(30) Foreign Application Priority Data

Mar. 9, 2012 (KR) .......................... 10-2012-0024588

(51) Int. Cl.
| | | |
|---|---|---|
| *A61K 47/40* | (2006.01) | |
| *A61K 47/10* | (2006.01) | |
| *A61K 31/728* | (2006.01) | |
| *A61K 31/5415* | (2006.01) | |
| *A61K 9/00* | (2006.01) | |

(52) U.S. Cl.
CPC ............... *A61K 47/40* (2013.01); *A61K 9/0019* (2013.01); *A61K 31/5415* (2013.01); *A61K 31/728* (2013.01); *A61K 47/10* (2013.01)

(58) Field of Classification Search
CPC ... A61K 47/40; A61K 47/10; A61K 31/5415; A61K 31/728
See application file for complete search history.

(56) References Cited

U.S. PATENT DOCUMENTS

| | | | |
|---|---|---|---|
| 4,434,163 A | 2/1984 | Lombardino | |
| 4,603,123 A | 7/1986 | Chiesi et al. | |
| 5,646,131 A | 7/1997 | Badwan et al. | |
| 6,017,900 A * | 1/2000 | Falk .................... | A61K 9/0014 424/427 |
| 2007/0270379 A1 | 11/2007 | Freiss et al. | |

FOREIGN PATENT DOCUMENTS

| | | |
|---|---|---|
| EP | 0 066 458 | 12/1982 |
| EP | 0 795 329 | 9/1997 |
| KR | 1985-000104 | 10/1987 |
| KR | 1986-0004782 | 1/1990 |
| KR | 1989-0008200 | 8/1992 |
| KR | 1992-0012790 | 9/1995 |
| WO | WO-97/24111 | 7/1997 |

OTHER PUBLICATIONS

Ming Guan Piao, et al., "Enhanced Oral Bioavailability of Piroxicam in Rats by Hualuronate Microspheres", Drug Development and Industrial Pharmachy, 33:485-491, 2007.
Jeung Tak Sub, "Clinical Importance and Application of Hyaluronic Acid", Korean Acad Fam Med vol. 23, No. 9, Sep. 2002, pp. 1071-1079.
Dung Chul Lee, et al., "Effect of the Hyaluronic Acid on Osteoarthritis of the Knee", Journal of Korean Knee Society, vol. 147, No. 2, Dec. 2002, pp. 213-221.
Yeon Wook Song, "Pharmacological Therapy in Osteoarthritis", Journal of Korean Medical Association 2003; 46 (11), pp. 958-964.
Seung Sook Noh, et al., "Efficacy of Intra-articular Sodium Hyaluronate in Patients with Osteoarthritis of the Knee", Korean J Paoin vol. 17, No. 2, 2004, pp. 170-174.
Sang Chul Lee, et al., "Raoud analgesic onset of intra-articular hyaluronic acid with ketorolac in osteoarthritis of the knee", Journal of Back and Musculoskeletal Rehabilitation 24 (2011) pp. 31-38.
Seval Izdes, et al., "The Effects of Preoperative Inflammation of the Analgesic Efficacy of Intraarticular Piroxicam for Outpatient Knee Arthroscopy", Anesth Analg 2003; 97, pp. 1016-1019.

* cited by examiner

*Primary Examiner* — Jonathan S Lau
(74) *Attorney, Agent, or Firm* — Norris McLaughlin & Marcus, P.A.

(57) ABSTRACT

The present invention relates to a novel liquid composition comprised of piroxicam or its pharmaceutically acceptable salt (a non-steroid anti-inflammatory drug) and hyaluronic acid or its pharmaceutically acceptable salt (used for treatment of degenerative arthritis). Specifically, the invention provides a highly physicochemically stable liquid injection, comprising piroxicam and hyaluronic acid as active ingredients and β-cyclodextrin or its derivative and polyethylene glycol as additives to enhance its physicochemical stability, and the preparation method thereof.

14 Claims, No Drawings

STABLE LIQUID PHARMACEUTICAL COMPOSITION CONTAINING PIROXICAM OR ITS PHARMACEUTICALLY ACCEPTABLE SALT AND HYALURONIC ACID OR ITS PHARMACEUTICALLY ACCEPTABLE SALT AND THE MANUFACTURING METHOD THEREOF

TECHNICAL FIELD

This invention pertains to a physicochemically stabilized, novel pharmaceutical liquid composition of poorly water-soluble piroxicam or its pharmaceutically acceptable salt and redox-unstable hyaluronic acid and its pharmaceutically acceptable salt, and the manufacturing method thereof.

BACKGROUND ART

Polymeric hyaluronic acid or its pharmaceutically acceptable salt is used to treat degenerative arthritis, rheumatoid arthritis, and their likes. Hyaluronic acid or its salt is commonly prepared in the form of a liquid injection and is administered directly to the affected joint such as the knee and the shoulder. It is reported that the viscoelastic polymer substance is directly injected into the articular cavity of an arthritis patient to relieve the shock felt upon joint movement due to the lost cartilage tissue, as well as to facilitate lubrication, thus alleviating joint pains, normalizing functions, as well as improving arthritis-caused dysfunctions and inhibiting pains. (Jeung Tak Suh, Clinical importance and application of hyaluronic acid. *Korean Journal of Family Medicine* 2002; 23(9): 1071-1079; Dong Chul Lee, Seung Hee Back, Wook Jin Sohn et al. Effect of the hyaluronic acid on osteoarthritis of the knee. *Journal of Korean Knee Society* 2002; 14(2): 213-221; Yeong Wook Song. Pharmacological therapy in osteoarthritis. *Journal of Korean Medical Association* 2003; 46(11): 958-964; Seung Sook No, Jae Jun Lee, Sung Mi Hwang et al. Efficacy of intra-articular sodium hyaluronate in patients with osteoarthritis of the knee. The Korean *Journal of Pain* 2004; 17(2): 170-174).

According to literature reports, it has been shown that administration of hyaluronic acid in combination with certain types of nonsteroidal anti-inflammatory drugs (NSAIDs) directly to the articular cavity can improve the effects of the hyaluronic acid injection. (S C Lee, D W Rha. W H Chang. Rapid analgesic onset of intra-articular hyaluronic acid with ketorolac in osteoarthritis of the knee. *J. Back Musculoskeletal Rehabilitation* 2011; 24:31-38).

Piroxicam, a nonsteroidal anti-inflammatory drug of the benzothiazine derivative class, produces its anti-inflammatory effect by inhibiting prostaglandin synthesis, and is currently used to treat degenerative arthritis for its outstanding analgesic and anti-inflammatory actions as well as the long plasma half-life. It has been demonstrated to show excellent topical anti-inflammatory and analgesic effects, and furthermore, it has been reported that the drug, upon direct intraarticular injection, effectively removes inflammation (Izdes S, Orhun S, Turanli S, Erkilic E, Kanbak O. The effects of preoperative inflammation on the analgesic efficacy of intraarticular piroxicam for outpatient knee arthroscopy *Anesth Analg* 2003; 97(4):1016-1019).

Piroxicam injections (e.g. Felaxicam injection, Dream Pharma Corp., intramuscular injection) or injections of its salts (e.g. Rheoma injection, Sam Sung Pharmaceutical Ind. Co., Ltd., intramuscular injection) currently on the market are alkaline aqueous solutions of pH 8.5 or above, and thus pose the problem of easily producing crystallization or turbidity in the pH range falling outside of the alkaline solution (due to their instability in such an environment). Moreover, direct injection of the alkaline solution of pH 8.5 or above containing piroxicam or its salt to the diseased area including joints and shoulders may induce irritation within the tissue, such as pain, inflammation, or edema.

Furthermore, hyaluronic acid is reported to exhibit decrease in molecular size and drop in viscosity upon oxidation-reduction reaction or chain hydrolysis reaction, thus requiring lightproof refrigerated storage. Particularly, it is reported that the decomposition may accelerate in a strong acidic or strong alkaline aqueous solution. Viscosity has a direct effect on the therapeutic action of hyaluronic acid or its salt; decrease in viscosity is reported to cause a rapid reduction of its pharmacological action.

For these reasons, simply adding hyaluronic acid or it salt to the intramuscular injection of the existing piroxicam or its salt and directly administering the product to the lesion poses many pharmaceutically problematic consequences. Therefore, in order to manufacture an aqueous solution of the combination of piroxicam or its salt and hyaluronic acid or its salt, a pharmaceutical composition is required that is highly compatible with both hyaluronic acid and piroxicam, and is able to improve the physicochemical stability of hyaluronic acid and piroxicam.

Korean Patent Application No. 1992-12790 discloses the injectable pharmaceutical composition of piroxicam potassium, containing piroxicam potassium, lidocaine, triethylene glycol and sterile water for injections. According to the above-identified patent application (Example 2), the drug is soluble only in the alkaline condition of pH equal to or exceeding 8.5 despite the solvent comprising 40% wt of the composition, and a pH of 7.4 or below caused a problem of formation of piroxicam potassium precipitation. Also in particular, it is pointed out that mixing sodium hyaluronate reduces the stability of hyaluronic acid.

Korean Patent Application No. 1986-4782 discloses the method of manufacturing the injections by dissolving an alkali metal salt of piroxicam in water and applying 30-80% wt of propylene glycol, polyethylene glycol, and dimethylacetamide per principal ingredient. However, dimethylacetamide included in the above-mentioned patent application is a highly toxic solvent with a margin of exposure of 10.9 mg per day and whose use at present time is strictly limited, thereby deemed problematic to administer to a diseased area.

Korean Patent Application No. 1989-8200 discloses the injectable composition comprising piroxicam and solubilizing agent of 1.1-1.2 mole of L-arginine or L-lysine, propylene glycol and povidone per 1 mole of piroxicam. The Examples 1-5 is soluble only in pH of 8.0 or above and a problem of a decrease in physical stability in pH of 7.4 or below is seen. Mixing sodium hyaluronate poses the problem of significantly decreasing the stability of hyaluronic acid.

U.S. Pat. No. 4,434,163 and European Patent No. 66458 describe allowing piroxicam to react with L-arginine, producing an arginine salt of piroxicam, and mixing the product with disodium hydrogen phosphate ($Na_2HPO_4$) to generate a vial filled with injectable powder. However, such an injectable powder, once dissolved in aqueous solution, generates crystal deposits when stored at room temperature for two or more days. This phenomenon makes its long-term storage in the liquefied form impossible, thus presenting a drawback of requiring immediate use.

Korean Patent Application No. 1985-1074 has demonstrated successfully the enhancement of solubility of piroxicam by adding cyclodextrin. However, said technique involves spray-drying or freeze-drying procedures, making it a complicated manufacturing process. Furthermore, these techniques are used to enable oral administration of piroxicam, including tablets, and possess drawbacks of generating precipitation extracts upon long-term storage in aqueous solution, as well as insufficient stability.

U.S. Pat. No. 5,646,131 and U.S. Published Application No. 2007/0270379 have successfully enhanced the solubility of piroxicam using cyclodextrin in combination with hydroxy-carboxylic acid or arginine. However, said technique is designed for oral administration of piroxicam including tablets, and possess the drawbacks of generating precipitation extracts upon long-term storage in aqueous solution as well as insufficient stability.

As shown above, the present inventor has identified that, from the existing prior art, one cannot manufacture a complex composition combining piroxicam and hyaluronic acid as active ingredients. Accordingly, in efforts to develop a stable liquid composition containing piroxicam or its pharmaceutically acceptable salt and hyaluronic acid or its pharmaceutically acceptable salt, the inventor has tested various pharmaceutically acceptable common solubilizing agents, stabilizing agents, solvents, and the likes, culminating in the completion of the present invention.

DISCLOSURE

Technical Problem

The objective of the present invention is to provide a novel pharmaceutical liquid composition physicochemically stabilizing the poorly water-soluble piroxicam or its pharmaceutically acceptable salt and the redox-unstable hyaluronic acid or its pharmaceutically acceptable salt, and a preparation method thereof.

Technical Solution

In order to achieve the objective above, the present invention provides a novel, physicochemically stabilized pharmaceutical liquid composition of piroxicam or its pharmaceutically acceptable salt and hyaluronic acid or its pharmaceutically acceptable salt, and a preparation method thereof.

The following is a detailed description of the present invention:

The present invention provides a new, physicochemically stabilized pharmaceutical liquid composition of piroxicam or its pharmaceutically acceptable salt and hyaluronic acid or its pharmaceutically acceptable salt.

The new pharmaceutical liquid composition in accordance with the present invention comprises piroxicam, an anti-inflammatory analgesic, and hyaluronic acid as active ingredients, and β-cyclodextrin and polyethylene glycol as stabilizing agents.

Unless otherwise specified in the present invention, piroxicam, hyaluronic acid, β-cyclodextrin, and polyethylene glycol are hereinafter defined as the following:

"Piroxicam" in the present invention refers to piroxicam as such or its pharmaceutically acceptable salt. A pharmaceutically acceptable salt of piroxicam is an organic or inorganic addition salt of piroxicam at a concentration relatively non-toxic, harmless, and effective to patients, and the side effects of which do not degrade the beneficial effects of the piroxicam salt. Such a salt may use inorganic acid or organic acid as a free acid. Acceptable inorganic acids include hydrochloric acid, bromic acid, nitric acid, sulfuric acid, perchloric acid, and phosphoric acid; and such organic acids include citric acid, acetic acid, lactic acid, maleic acid, fumaric acid, gluconic acid, glyconic acid, succinic acid, tartaric acid, galacturonic acid, embonic acid, glutamic acid, aspartic acid, oxalic acid, D-malic acid or L-malic acid, methanesulfonic acid, ethanesulfonic acid, 4-toluenesulfonic acid, salicylic acid, citric acid, benzoic acid, malonic acid. Such salts also include alkali metallic salts (e.g. sodium salts, potassium salts) and alkali earth metallic salts (e.g. calcium salts, magnesium salts). For example, acid addition salts may include acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/bihydrogen phosphate, saccharate, stearate, succinate, tartrate, tosylate, trifluoroacetate, aluminum, arginine, benzatine, calcium, choline, diethylamine, diolamine, glycine, lysine, magnesium, meglumine, olamine, potassium, sodium, tromethamine, zinc salts, and their likes. Advisably, alkali metallic salts, amines, and amino acid salts such as arginine and lysine may be used.

A piroxicam salt, generated with one of the aforementioned acceptable salts, may be used to initiate formulation of the above-mentioned composition. Alternatively, aforementioned acceptable salts may be added midway in the formulation process, at the time of dissolving piroxicam with 1-cyclodextrin and polyethylene glycol in a solvent, and followed by sufficient stirring, to generate piroxicam salt.

In the present invention, "hyaluronic acid" is defined to include hyaluronic acid as such as well as its pharmaceutically acceptable salt. In other words, "hyaluronic acid" as referred to in the present invention includes hyaluronic acid, hyaluronate salt, and mixture of hyaluronic acid and hyaluronate salt. Hyaluronate salts include inorganic salts such as sodium hyaluronate, magnesium hyaluronate, zinc hyaluronate, and cobalt hyaluronate, and organic salts such as tetrabutylammonium hyaluronate. If required, two or more of the aforementioned compounds can be used. Although the molecular weight of hyaluronic acid in the present invention is not particularly limited, its advisable range is between 500,000 and 10,000,000.

As stabilizing agents in the composition of the injection in the present invention, β-cyclodextrin or its derivative and polyethylene glycol are used, and their amount used can vary by the weight of the active ingredients, the pH of the injection, and the ratio of the two diluting agents.

Notably, no beneficial effect was observed when stabilizing agents other than β-cyclodextrin and polyethylene glycol were used, either separately or in a mixture with β-cyclodextrin or its derivative. Rather, phase separation of hyaluronic acid and decline in stability of piroxicam can be observed in such cases. Evaluated diluting agents include propylene glycol, polysorbate 20, 60 or 80, Cremophor® (RH40, RH60, EL), Brij® (Brij-58, Brij-52, Brij-700, Brij-76), saturated polyglycolyzed glyceride (proprietary name Gelucire® 44/14, 53/10, 50/13, 42/12 or 35/10), polyoxyethylene-polyoxypropylene copolymer or block copolymer (brand name Pluronic® or Poloxamer, Poloxamer 188), ethoxylated cholesterins (Solulan™) (e.g. Solulan C24), vitamin derivatives (Vitamin E derivatives such as tocopherol polyethylene glycol succinate (TPGS)), sodium dodecyl sulfate or sodium lauryl sulfate, bile acids or bile salts (e.g. cholic acid, glycolic acid, or sodium cholate), lecithin, glycerin, triethylene glycol, tetraglycol, alcohols (ethanol, butanol), Transcutol®, Solutol® HS15, sorbitol, N-methylpyrrolidone, and Kollidon® 12/17 PF.

Also, "β-cyclodextrin" in the present invention is defined to include β-cyclodextrin ether derivatives, examples of which are described in the U.S. Pat. No. 3,459,731 and others. Typically, these ethers or mixed ether derivatives comprise β-cyclodextrin whose one or more of hydroxyl groups are substituted with C1-6-alkyl, hydroxy-C1-6-alkyl, carboxy-C1-6-alkyl, and/or C1-6-alkyloxycarbonyl groups. An advisable such substituted 3-cyclodextrin may comprise one or more hydroxyl groups whose hydrogen is substituted C1-3-alkyl, hydroxy-C2-4-alkyl, carboxy-C1-2-alkyl group(s)— or more ideally, with methyl, ethyl, hydroxyethyl, hydroxypropyl, hydroxylbutyl, carboxymethyl or carboxyethyl group(s).

Above-mentioned β-cyclodextrin derivatives have a DS (degree of substitution, or the average number of substituted hydroxyl functional groups per glucose unit) value in the range of 0.125 to 3, and advisably from 0.3 to 2. The range of MS (molar substitution, or the average number of moles of substituents per glucose unit) is from 0.125 to 10, and advisably from 0.3 to 3. Furthermore, one or more hydroxyl groups may be substituted by sugar groups, such as maltosyl, glucosyl, and maltotriosyl groups. One or more sulfoalkyl C1-4-ether substituent may be added to the β-cyclodextrin. In this case, either sulfopropyl ether β-cyclodextrin or sulfobutyl ether β-cyclodextrin is suitable.

Examples of β-cyclodextrin substituents suitable for this invention include 2,6-dimethyl-β-cyclodextrin, 2-hydroxyethyl-β-cyclodextrin, 2-hydroxypropyl-β-cyclodextrin, (2-carboxymethoxy)propyl-β-cyclodextrin, and sulfobutyl ether(7) β-cyclodextrin, and the most suitable among these is hydroxypropyl-β-cyclodextrin.

The above-mentioned polyethylene glycol refer to those whose average molecular weight is in the range from 200 to 100,000 and whose structure includes a hydroxyl group at the terminal and another activating group—e.g. amine, carboxyl, hydroxyl, and thiol—for functional group. Such polymers of any molecular weight may be used; in particular, one whose average molecular weight is 400-10,000 is used. Branched polymers as well as linear polymers may be used.

Piroxicam and hyaluronic acid, the novel pharmaceutical active ingredients in accordance with the present invention, constitutes 0.5-10.0% wt and 0.5-5.0% wt of the composition, respectively. A suitable total weight of β-cyclodextrin and polyethylene glycol, the pharmaceutical additives, is 5-50 times the weight of total piroxicam in the injection solution.

Piroxicam or its salt may constitute 0.5-10.0% wt (as the concentration of free-base piroxicam) of the entire injection fluid. Its treatment effect is minimal below 0.5% wt, and at a level above 10.0% wt, it requires an excess amount of solubilizing agents, which may cause drifting of solubilizing agents or precipitation of piroxicam. Moreover, hyaluronic acid or its salt in the liquid composition may constitute 0.5-5.0% wt (as concentration of hyaluronic acid) of the entire aqueous solution. The treatment effect of hyaluronic acid is minimal at a concentration level below 0.5% wt, and a level above 5.0% wt results in a sharp increase in the viscosity of the composition, making it difficult to fill a pre-filled syringe or an ampoule container; it can also cause irritation when injecting to a patient's affected area.

Also, the stabilizing agents of the present invention can use a combination of β-cyclodextrin and polyethylene glycol from 5 to 50 times the weight of piroxicam or its salt. Using a smaller quantity can cause precipitation of piroxicam or its salt upon cold storage. A larger quantity may result in difficulty dissolving the above-mentioned diluting agent in a medium, and side effects can be caused by the excessive overdose of diluting agents on the human body. More advisably, 10 to 45 times of β-cyclodextrin and polyethylene glycol per weight of piroxicam may be used. As such in this present invention, the ratio between 3-cyclodextrin and polyethylene glycol is from 30:1 to 1:20, advisably from 15:1 to 1:10. Using the aforementioned ratios, the above-mentioned composition with excellent physicochemical stability and minimum amount of diluting agents can be developed.

Furthermore, the advisable pH of the liquid composition is from 5.5 to 8.5. Upon cold or room temperature storage at pH 5 or below, piroxicam's physical stability can decline and produce precipitation extracts. A pH level of 8.5 or above renders hyaluronic acid unstable, and intraarticular injection of the aforementioned liquid composition in this state may cause pain, edema, inflammation, and other side effects due to local irritation.

The liquid composition in accordance with the present invention may, if necessary due to its route of administration or dosage form, contain a suitable combination of suspending agents, solubilizing agents, stabilizing agents, isotonizing agents, preserving agents, adhesion-preventing agents, surfactants, diluents, excipients, pH adjusters, local anesthetics, buffers, sulfur-containing reducing agents, antioxidants, and other such additives. For example, it may consist of sterilized water, normal saline solution, common buffer (e.g. phosphoric acid, citric acid, other organic acid), stabilizers, salts, antioxidants (e.g. ascorbic acid), surfactants, suspending agents, isotonizing agents, and preserving agents. The composition's injectable aqueous solution form may be comprised of, for example, normal saline solution, isotonic solution containing glucose or other adjuvant drugs (e.g. D-sorbitol, D-mannose, D-mannitol, and sodium chloride), as well as buffers (e.g. phosphate buffer solution, sodium acetate buffer solution), local anesthetics (e.g. procaine hydrochloride), and stabilizers (e.g. benzyl alcohol, phenol, antioxidant). Pharmaceutically acceptable carriers and formulations suitable for the present invention are described in detail in the following reference: Remington's Pharmaceutical Sciences, 19$^{th}$ ed., 1995.

Also, the present invention provides preparation methods of the novel, physicochemically stabilized pharmaceutical liquid composition of piroxicam or its pharmaceutically acceptable salt and hyaluronic acid or its pharmaceutically acceptable salt. Namely, piroxicam or its pharmaceutically acceptable salt is mixed with β-cyclodextrin and polyethylene glycol in a solvent and sufficiently stirred to dissolution, and hyaluronic acid or its pharmaceutically acceptable salt is added to this solution and sufficiently stirred to dissolution, followed by the formulation of the injectable liquid composition via general ordinary methods of preparing injection fluids. For the solvent used in preparation of the liquid pharmaceutical composition of the present invention, it is advisable to use normal saline solution or sterile water for injection.

Advantageous Effects

Using the novel pharmaceutical liquid composition and the preparation methods thereof provided in the present invention enables formulation of physicochemically stabilized liquid injections comprising piroxicam or its pharmaceutically acceptable salt and hyaluronic acid or its pharmaceutically acceptable salt.

MODE FOR INVENTION

The present invention is hereunder described in greater detail with reference to examples in order to illustrate the principles of the present invention. However, these examples are subject to numerous modifications and changes, and shall not be interpreted to limit the scope of the present invention. These examples are provided only to completely describe the invention to those having ordinary skill in the art.

Examples 1-2

Liquid Compositions in Accordance with the Present Invention (1), Containing Hydroxypropyl-β-Cyclodextrin and Polyethylene Glycol as Stabilizing Agents 11.15 g of piroxicam potassium (10 g of piroxicam), 100 g of hydroxypropyl-β-cyclodextrin and 45 g of polyethylene glycol 4000 were added to approximately 350 Ml of phosphate buffered saline (pH 7.4). The mixture was stirred to dissolution at 30° C. for 1 hour, adjusted to either pH 8.0 (Example 1) or pH 7.0 (Example 2) with potassium hydroxide or 1N hydrochloric acid, and made into total volume of 500 Ml by adding sterile water for injection. The product was then sterilized with a syringe filter, and 5.0 g of sodium hyaluronate was added. Then the mixture was stirred for 12 hours at 30-40° C. with an overhead mixer to formulate liquid compositions.

TABLE 1

| | Piroxicam potassium (g) | HA (g) | HPBCD (g) | PEG 4000 (g) | Solution pH |
|---|---|---|---|---|---|
| Example 1 | 11.15 (2% of piroxicam) | 5.0 (1%) | 100.0 (20%) | 45.0 (9%) | 8.0 |
| Example 2 | 11.15 (2% of piroxicam) | 5.0 (1%) | 100.0 (20%) | 45.0 (9%) | 7.0 |

%: weight %
HA: sodium hyaluronate
HPBCD: hydroxypropyl-β-cyclodextrin

Examples 3-4

Liquid Compositions in Accordance with the Present Invention (2), Containing Hydroxypropyl-β-Cyclodextrin and Polyethylene Glycol as Stabilizing Agents According to the Present Invention 11.5 g of piroxicam potassium (10 g of piroxicam), 100 g of hydroxypropyl-β-cyclodextrin and 45 g of polyethylene glycol 4000 were added to approximately 350 Ml of phosphate buffered saline (pH 7.4). The mixture was stirred to dissolution for 1 hour at 30° C., and was set to a total volume of 500 Ml by adding buffered saline solution (Example 3) or by adding sterile water for injection after adjusted to pH 8.0 by potassium hydroxide (Example 4). It was then sterilized by a syringe filter, treated with 5.0 g of sodium hyaluronate, and stirred for 12 hours at 30-40° C. with an overhead mixer to formulate the liquid compositions.

TABLE 2

| | Piroxicam potassium (g) | HA (g) | HPBCD (g) | PEG 4000 (g) | Solution pH |
|---|---|---|---|---|---|
| Example 3 | 11.15 (2% of piroxicam) | 5.0 (1%) | 112.5 (22.5%) | 22.5 (4.5%) | 7.4 |

TABLE 2-continued

| | Piroxicam potassium (g) | HA (g) | HPBCD (g) | PEG 4000 (g) | Solution pH |
|---|---|---|---|---|---|
| Example 4 | 11.15 (2% of piroxicam) | 5.0 (1%) | 112.5 (22.5%) | 22.5 (4.5%) | 8.0 |

Examples 5-9

Liquid Compositions in Accordance with the Present Invention (3), Containing Hydroxypropyl-β-Cyclodextrin and Polyethylene Glycol as Stabilizing Agents According to the Present Invention The ingredients specified in Table 3 below were added to approximately 350 Ml of phosphate buffered saline (pH 7.4). The procedure described in Example 1 was carried out for each, to generate the liquid compositions of Examples 5-9, respectively.

TABLE 3

| | Piroxicam potassium (g) | HA (g) | HPBCD (g) | PEG 4000 (g) | Solution pH |
|---|---|---|---|---|---|
| Example 5 | 11.15 (2% of piroxicam) | 5.0 (1%) | 50.0 (10%) | 100.0 (20%) | 8.0 |
| Example 6 | 11.15 (2% of piroxicam) | 5.0 (1%) | 75.0 (15%) | 25.0 (5%) | 8.5 |
| Example 7 | 11.15 (2% of piroxicam) | 5.0 (1%) | 100.0 (20%) | 22.5 (4.5%) | 8.0 |
| Example 8 | 11.15 (2% of piroxicam) | 5.0 (1%) | 75.0 (15%) | 45.0 (9%) | 8.0 |
| Example 9 | 16.725 (3% of piroxicam) | 15.0 (3%) | 112.5 (22.5%) | 67.5 (13.5%) | 8.0 |

Example 10

A Liquid Composition in Accordance with the Present Invention (4), Containing Hydroxypropyl-β-Cyclodextrin and Polyethylene Glycol as Stabilizing Agents According to the Present Invention 5.0 g of piroxicam along with the ingredients specified in Table 4 below were added to approximately 350 Ml of phosphate buffered saline (pH 7.4). The mixture was subjected to the procedure described in Example 1 to formulate a liquid composition.

TABLE 4

| | Piroxicam | HA | HPBCD | PEG 4000 | Solution pH |
|---|---|---|---|---|---|
| Example 10 | 5.0 (1%) | 5.0 (1%) | 150.0 (30%) | 75.0 (15%) | 8.0 |

Examples 11-12

Liquid Compositions in Accordance with the Present Invention (5), Containing Hydroxypropyl-β-Cyclodextrin and Polyethylene Glycol as Stabilizing Agents According to the Present Invention 20.0 g of piroxicam, 12.0 g of L-arginine, 200 g of hydroxypropyl-β-cyclodextrin and 90 g of polyethylene glycol 4000 were added to approximately 700 Ml of phosphate buffered saline (pH 7.4). The mixture was stirred to dissolution for 1 hour at 30° C., adjusted to either pH 8.0 (Example 11) or pH 7.0 (Example 12) with potassium hydroxide or 1N hydrochloric acid, set to a total volume of 1,000M by adding sterile water for injection, and stirred thoroughly. It was then sterilized with a syringe filter, treated with 10.0 g of sodium hyaluronate, and stirred for 12 hours at 30-40° C. to form liquid compositions.

TABLE 5

|  | Piroxicam (g) | L-arginine (g) | HA (g) | HPBCD (g) | PEG 4000 (g) | Solution pH |
|---|---|---|---|---|---|---|
| Example 11 | 20.0 (2%) | 12.0 (1.2%) | 10.0 (1%) | 200.0 (20%) | 90.0 (9%) | 8.0 |
| Example 12 | 20.0 (2%) | 12.0 (1.2%) | 10.0 (1%) | 200.0 (20%) | 90.0 (9%) | 7.0 |

Examples 13-14

Liquid Compositions in Accordance with the Present Invention (6), Containing Hydroxypropyl-β-Cyclodextrin and Polyethylene Glycol as Stabilizing Agents According to the Present Invention 200.0 g of Arginine salt of piroxicam (20.0 g of piroxicam), 200.0 g of hydroxypropyl-β-cyclodextrin and 90 g of polyethylene glycol 4000 were added to approximately 700 Ml of phosphate buffered saline (pH 7.4) and were dissolved at 30° C. by stirring for 1 hour. The mixture was then adjusted to either pH 8.0 (Example 13) or pH 7.0 (Example 14) with potassium hydroxide or 1N hydrochloric acid, set to a total volume of 1,000 Ml by adding sterile water for injection, thoroughly mixed, sterilized with a syringe filter, and treated with 5.0 g of sodium hyaluronate. The solution was stirred for 12 hours with an overhead mixer at 30-40° C. to form the liquid compositions.

TABLE 6

|  | Arginine salt of piroxicam (g) | HA (g) | HPBCD (g) | PEG4000 (g) | Solution pH |
|---|---|---|---|---|---|
| Example 13 | 30.6 (2% of piroxicam) | 10.0 (1%) | 200.0 (20%) | 90 (9%) | 8.0 |
| Example 14 | 30.6 (2% of piroxicam) | 10.0 (1%) | 200.0 (20%) | 90 (9%) | 7.0 |

Comparative Example 1

A Liquid Composition without a Stabilizing Agent 5 g of sodium hyaluronate and 11.15 g of piroxicam potassium were added to 500 Ml of phosphate buffered normal saline (pH 7.4). The mixture was stirred for 12 hours with an overhead mixer at 30-40° C. to formulate a liquid composition.

TABLE 7

|  | Piroxicam potassium (g) | HA (g) | Solution pH |
|---|---|---|---|
| Comparative Example 1 | 11.15 (2% of piroxicam) | 5.0 (1%) | 7.4 |

Comparative Example 2-3

Liquid Compositions Containing Propylene Glycol and Povidone as Stabilizing Agents 20 g of piroxicam, 12 g of L-arginine, and 200 g of propylene glycol were added to 700 Ml sterile water for injection at 70° C. The mixture was stirred to dissolution for 30 minutes, and then treated with 10 g of povidone (Polyvinylpyrrolidine K-30) and 10 g of benzene alcohol. Following 10 minutes of stirring, the mixture was cooled down to room temperature, adjusted to either pH 8.3 (Comparative Example 2) or pH 7.0 (Comparative Example 3) with potassium hydroxide or 1N hydrochloric acid, made into a total volume of 1000 Ml by adding sterile water for injection, and thoroughly mixed. The product was subjected to sterile filtration, treated with 10.0 g of sodium hyaluronate, and stirred for 12 hours with an overhead mixer at 30-40° C. to formulate liquid compositions.

TABLE 8

|  | Piroxicam (g) | L-arginine (g) | HA (g) | Povidone (g) | Propylene glycol (g) | Benzyl alcohol (g) | Solution pH |
|---|---|---|---|---|---|---|---|
| Comparative Example 2 | 20.0 (2% of piroxicam) | 12.0 (1.2%) | 10.0 (1%) | 10.0 (1%) | 200.0 (20%) | 10 (1%) | 8.3 |
| Comparative Example 3 | 20.0 (2% of piroxicam) | 12.0 (1.2%) | 10.0 (1%) | 10.0 (1%) | 200.0 (20%) | 10 (1%) | 7.0 |

Comparative Examples 4-5

Liquid Compositions Containing Triethylene Glycol as a Stabilizing Agent 22.3 g of piroxicam potassium was added to and completely dissolved in 400 Ml of sterile water for injection. Separately, 10 g of lidocaine was added to and completely dissolved in 400 Ml of triethylene glycol. The piroxicam potassium solution was gradually stir-mixed into the lidocaine-dissolved triethylene glycol solution, and a small amount of sterile water for injections was used to rinse the container and then added to the mixture. The mixed solution was then adjusted to either pH 8.5 (Comparative Example 4) or pH 7.0 (Comparative Example 5) with potassium hydroxide or 1N hydrochloric acid and made into exactly 1,000 Ml by adding sterile water for injection. It was then prepared following the method designed in the General Requirements for Pharmaceutical Preparations according to the Korean Pharmacopoeia. It was treated with 10.0 g of sodium hyaluronate, and stirred for 12 hours with an overhead mixer at 30-40° C. to formulate liquid compositions.

TABLE 9

|  | Piroxicam potassium (g) | HA (g) | Lidocaine (g) | Triethylene glycol (Ml) | Solution pH |
|---|---|---|---|---|---|
| Comparative Example 4 | 22.3 (2%) | 10.0 (1%) | 10.0 (1%) | 400.0 (40%) | 8.5 |
| Comparative Example 5 | 22.3 (3%) | 10.0 (1%) | 10.0 (1%) | 400.0 (40%) | 7.0 |

Comparative Example 6

A Liquid Composition Containing Only β-Cyclodextrin as a Stabilizing Agent 500 mg of piroxicam and 4.26 g of β-cyclodextrin were dissolved in 1,000 of water at 60° C. The mixture was stirred at room temperature for 3 hours and cooled to 3° C. The product was separated via crystallization to generate a piroxicam-β-cyclodextrin complex. The complex was added to phosphate buffered saline and was stirred to make an aqueous solution of piroxicam with the piroxicam concentration of 20 mg/Ml. Sodium hyaluronate (amount corresponding to 1% concentration of the solution) was dissolved to formulate a liquid composition.

TABLE 10

|  | Piroxicam (g) | HA (g) | β-cyclodextrin (g) | Solution pH |
|---|---|---|---|---|
| Comparative Example 6 | 0.5 (2% of piroxicam) | 0.25 (1%) | 4.26 (17.04%) | 7.4 |

Comparative Examples 7 and 8

Liquid Compositions Containing Only Hydroxypropyl-β-Cyclodextrin as a Stabilizing Agent 22.3 g of piroxicam potassium (20.0 g of piroxicam) and 200 g of hydroxypropyl-β-cyclodextrin were added to approximately 700 Ml of phosphate buffered saline (pH 7.4). The mixture was stirred to complete dissolution at 30° C. for 1 hour, adjusted to either pH 8.0 (Comparative Example 7) or pH 7.0 (Comparative Example 8) with potassium hydroxide or 1N hydrochloric acid, and made into total volume of 1,000 Ml by adding sterile water for Injection, and well-stirred. It was sterilized with a syringe filter, treated with 10.0 g of sodium hyaluronate, and stirred for 12 hours at 30-40° C. with an overhead mixer to formulate liquid compositions.

TABLE 11

|  | Piroxicam potassium (g) | HA (g) | HPBCD (g) | Solution pH |
|---|---|---|---|---|
| Comparative Example 7 | 22.3 (2% of piroxicam) | 10.0 (1%) | 200.0 (20%) | 8.0 |
| Comparative Example 8 | 22.3 (2% of piroxicam) | 10.0 (1%) | 200.0 (20%) | 7.0 |

Comparative Examples 9-10

Liquid Compositions Containing Only Polyethylene Glycol as a Stabilizing Agent 22.3 g of piroxicam potassium (20.0 g of piroxicam) and 200 g of polyethylene glycol 4000 were added to approximately 700 Ml of phosphate buffered saline (pH 7.4). The mixture was stirred at 30° C. for 1 hour until completely dissolved, was adjusted to either pH 8.0 (Comparative Example 9) or pH 7.0 (Comparative Example 10) with potassium hydroxide or 1N hydrochloric acid, and was made into total volume of 1,000 Ml by adding sterile water for injection, followed by thorough stirring. After the product was sterilized with a syringe filter, 10.0 g of sodium hyaluronate was added. The mixture was stirred with an overhead mixer at 30-40° C. for 12 hours to formulate liquid compositions.

TABLE 12

|  | Piroxicam potassium (g) | HA (g) | PEG4000 (g) | Solution pH |
|---|---|---|---|---|
| Comparative Example 9 | 22.3 (2% of piroxicam) | 10.0 (1%) | 200.0 (20%) | 8.0 |
| Comparative Example 10 | 22.3 (2% of piroxicam) | 10.0 (1%) | 200.0 (20%) | 7.0 |

Comparative Examples 11 to 30

Liquid Compositions Containing Other Diluting Agents as a Stabilizing Agent 11.15 g of piroxicam potassium (10.0 g of piroxicam) and 200 g of each diluting agent as specified in Table 13 below were added to approximately 700 Ml of phosphate buffered saline (pH 7.4). The mixture was stirred at 30° C. for 1 hour, adjusted to pH 7.4, and made into total volume of 1,000 Ml by adding sterile water for injection. After the product was stirred well and was sterilized with a syringe filter, 10.0 g of sodium hyaluronate was added. It was stirred with an overhead mixer at 30-40° C. for 12 hours to formulate liquid compositions of Comparative Examples 11 to 30, respectively.

TABLE 13

| | Piroxicam potassium (g) | HA (g) | Stabilizing agent (g) | Solution pH |
|---|---|---|---|---|
| Comparative Example 11 | 11.15 (1% of piroxicam) | 10.0 (1%) | Polysorbate 80 200.0 (20%) | 7.4 |
| Comparative Example 12 | 11.15 (1% of piroxicam) | 10.0 (1%) | Poloxamer 188 200.0 (20%) | 7.4 |
| Comparative Example 13 | 11.15 (1% of piroxicam) | 10.0 (1%) | Poloxamer 407 200.0 (20%) | 7.4 |
| Comparative Example 14 | 11.15 (1% of piroxicam) | 10.0 (1%) | Cremophor EL 200.0 (20%) | 7.4 |
| Comparative Example 15 | 11.15 (1% of piroxicam) | 10.0 (1%) | Cremophor RH40 200.0 (20%) | 7.4 |
| Comparative Example 16 | 11.15 (1% of piroxicam) | 10.0 (1%) | Brij 35 200.0 (20%) | 7.4 |
| Comparative Example 17 | 11.15 (1% of piroxicam) | 10.0 (1%) | Brij 97 200.0 (20%) | 7.4 |
| Comparative Example 18 | 11.15 (1% of piroxicam) | 10.0 (1%) | Myrj 52 200.0 (20%) | 7.4 |
| Comparative Example 19 | 11.15 (1% of piroxicam) | 10.0 (1%) | Tocopheryl polyethylene glycol succinate (TPGS) 200.0 (20%) | 7.4 |
| Comparative Example 20 | 11.15 (1% of piroxicam) | 10.0 (1%) | Sodium lauryl Sulfate 200.0 (20%) | 7.4 |
| Comparative Example 21 | 11.15 (1% of piroxicam) | 10.0 (1%) | Ethanol 200.0 (20%) | 7.4 |
| Comparative Example 22 | 11.15 (1% of piroxicam) | 10.0 (1%) | Transcutol P 200.0 (20%) | 7.4 |
| Comparative Example 23 | 11.15 (1% of piroxicam) | 10.0 (1%) | Tetraglycol 200.0 (20%) | 7.4 |
| Comparative Example 24 | 11.15 (1% of piroxicam) | 10.0 (1%) | Solutol HS15 200.0 (20%) | 7.4 |
| Comparative Example 25 | 11.15 (1% of piroxicam) | 10.0 (1%) | Glycerin 200.0 (20%) | 7.4 |
| Comparative Example 26 | 11.15 (1% of piroxicam) | 10.0 (1%) | Sorbitol 200.0 (20%) | 7.4 |
| Comparative Example 27 | 11.15 (1% of piroxicam) | 10.0 (1%) | Kollidon 12 PF 200.0 (20%) | 7.4 |
| Comparative Example 28 | 11.15 (1% of piroxicam) | 10.0 (1%) | Kollidon 17 PF 200.0 (20%) | 7.4 |
| Comparative Example 29 | 11.15 (1% of piroxicam) | 10.0 (1%) | Lecithin 200.0 (20%) | 7.4 |
| Comparative Example 30 | 11.15 (1% of piroxicam) | 10.0 (1%) | Gelucire 44/14 200.0 (20%) | 7.4 |

Experimental Example 1

Examination of Stability Under Refrigeration

30 Ml of each of the liquid compositions of Examples 1 through 14 and Comparative Examples 1 through 30 was filled into a 50 Ml brown vial and stored under the refrigerated conditions (below 2-7° C.), as they were being examined for crystallizations, changes in pH, and uniformity. The results are recorded in Table 14.

As demonstrated in Table 14, Comparative Example 1, which contained no stabilizing agents, showed significantly decreased stability immediately after being refrigerated, forming precipitates. Comparative Examples 6 through 10, which contained either β-cyclodextrin or polyethylene glycol alone as a sole stabilizing agent comprising the present invention, generated precipitation extracts and caused changes in pH.

Strikingly, the liquid compositions of Examples 1 through 14, which contained appropriate proportion of β-cyclodextrin and polyethylene glycol as stabilizing agents according to the present invention, showed no signs of precipitation or pH changes even after 3 months of refrigeration.

In contrast, as for Comparative Examples 2 through 5 containing stabilizing agents other than the those according to the present invention, the liquid compositions prepared with propylene glycol and povidone (Comparative Examples 2 and 3) as well as those with triethylene glycol (Comparative Examples 4 and 5) exhibited pH-dependent precipitation, thus indicating that for the prior patent inventions, their physical stability was very sensitive to pH changes, making it impossible to prepare stable liquid compositions of piroxicam in a physiologically stable condition.

Furthermore, upon examining the results of other stabilizing agents, it was observed that using poloxamer 188 (Comparative Example 12), poloxamer 407 (Comparative Example 13), Cremophor EL (Comparative Example 14), Cremophor RH40 (Comparative Example 15), Brij 35 (Comparative Example 16), and tocopheryl polyethylene glycol succinate (Comparative Example 19) as stabilizing agents resulted in the formation of separation of layers, making it impossible to prepare liquid compositions containing piroxicam and hyaluronic acid. And in the cases where other stabilizing agents were used, stability decreased significantly due to the formation of precipitation immediately after refrigeration, as in Comparative Example 1 which contained no stabilizing agents.

TABLE 14

Examination results of stability under refrigeration

| | Formation of Precipitation | | | |
|---|---|---|---|---|
| | Immediately after | 15 days | 1 month | 3 months |
| Example 1 | – | – | – | – |
| Example 2 | – | – | – | – |
| Example 3 | – | – | – | – |
| Example 4 | – | – | – | – |
| Example 5 | – | – | – | – |
| Example 6 | – | – | – | – |
| Example 7 | – | – | – | – |
| Example 8 | – | – | – | – |
| Example 9 | – | – | – | – |
| Example 10 | – | – | – | – |
| Example 11 | – | – | – | – |
| Example 12 | – | – | – | – |
| Example 13 | – | – | – | – |
| Example 14 | – | – | – | – |
| Comparative Example 1 | +++ | +++ | +++ | +++ |
| Comparative Example 2 | – | – | – | – |
| Comparative Example 3 | – | + | ++ | ++ |
| Comparative Example 4 | – | – | – | – |
| Comparative Example 5 | – | + | ++ | +++ |
| Comparative Example 6 | + | +++ | +++ | +++ |
| Comparative Example 7 | – | + | + | ++ |
| Comparative Example 8 | + | +++ | +++ | +++ |
| Comparative Example 9 | – | +++ | +++ | +++ |
| Comparative Example 10 | + | ++ | ++ | ++ |
| Comparative Example 11 | +++ | +++ | +++ | +++ |
| Comparative Example 12 | Separation of layers | Separation of layers | Separation of layers | Separation of layers |
| Comparative Example 13 | Separation of layers | Separation of layers | Separation of layers | Separation of layers |
| Comparative Example 14 | Separation of layers | Separation of layers | Separation of layers | Separation of layers |
| Comparative Example 15 | Separation of layers | Separation of layers | Separation of layers | Separation of layers |

TABLE 14-continued

Examination results of stability under refrigeration

Formation of Precipitation

| | Immediately after | 15 days | 1 month | 3 months |
|---|---|---|---|---|
| Comparative Example 16 | Separation of layers | Separation of layers | Separation of layers | Separation of layers |
| Comparative Example 17 | +++ | +++ | +++ | +++ |
| Comparative Example 18 | +++ | +++ | +++ | +++ |
| Comparative Example 19 | Separation of layers | Separation of layers | Separation of layers | Separation of layers |
| Comparative Example 20 | +++ | +++ | +++ | +++ |
| Comparative Example 21 | +++ | +++ | +++ | +++ |
| Comparative Example 22 | +++ | +++ | +++ | +++ |
| Comparative Example 23 | +++ | +++ | +++ | +++ |
| Comparative Example 24 | +++ | +++ | +++ | +++ |
| Comparative Example 25 | +++ | +++ | +++ | +++ |
| Comparative Example 26 | +++ | +++ | +++ | +++ |
| Comparative Example 27 | +++ | +++ | +++ | +++ |
| Comparative Example 28 | +++ | +++ | +++ | +++ |
| Comparative Example 29 | +++ | +++ | +++ | +++ |
| Comparative Example 30 | +++ | +++ | +++ | +++ |

Experimental Example 2

Examination of Stability at 80° C.

30 Ml of each of the liquid compositions of Examples 1 to 2 as well as that of Comparative Examples 1 through 10 was filled into 50 Ml brown vials and were stored under a stress condition (80° C.) as they were being examined for changes in properties, piroxicam contents and viscosity of compositions. The piroxicam contents were measured by high performance liquid chromatography, and the changes in viscosity of compositions were examined by utilizing capillary viscometer (Viscosystem AVS470 model) of sodium hyaluronate formulation according to the regulations set by the EP. They were kept under the 80° C. storage condition and were examined after the predetermined time. The results were recorded in Table 15.

As demonstrated in Table 15, in Comparative Example 1 containing no stabilizing agents, the degree of viscosity decline of sodium hyaluronate when stored under the stress condition was comparable to that of the Examples. However, precipitates started to form after 72 hours.

Furthermore, for Comparative Examples 6 through 8 containing β-cyclodextrin as a sole stabilizing agent, each of them showed changes in piroxicam contents according to time and for Comparative Examples 9 and 10 containing polyethylene glycol as a sole stabilizing agent, stability of piroxicam improved in Comparative Example 9 whereas precipitation was formed in Comparative Example 10.

In contrast, Examples 1 and 2 in accordance of the present invention, which contained both β-cyclodextrin and polyethylene glycol, showed the most superior stability under the stress condition, and the degree of decrease in viscosity of sodium hyaluronate was very favorable.

On the other hand, as for Comparative Examples 2 through 5 containing stabilizing agents other than those according to the present invention, over 10% change in the piroxicam content was observed when propylene glycol was used as a stabilizing agent (Comparative Examples 2 and 3). Particularly, the liquid compositions that contained triethylene glycol (Comparative Example 4 and 5) exhibited the problem of piroxicam itself failing to dissolve in the solvent.

TABLE 15

Examination results of stability at 80° C.

| | Changes in viscosity of HA (with respect to it being opened) | | Contents of piroxicam K (with respect to it being opened) | |
|---|---|---|---|---|
| | After 48 hours | After 120 hours | After 72 hours | After 240 hours |
| Example 1 | 81.4% | 62.5% | 99.9% | 95.4% |
| Example 2 | 80.1% | 59.6% | 100.1% | 94.5% |
| Comparative Example 1 | 79.9% | 60.9% | precipitation | precipitation |
| Comparative Example 2 | 54.5% | 19.7% | 94.8% | 80.3% |
| Comparative Example 3 | 60.1% | 18.8% | 95.0% | 82.6% |
| Comparative Example 4 | 72.4% | 47.5% | 97.2% | 88.1% |
| Comparative Example 5 | 68.6% | 39.6% | precipitation | precipitation |
| Comparative Example 6 | — | — | precipitation | precipitation |
| Comparative Example 7 | — | — | 95.7% | 88.6% |
| Comparative Example 8 | — | — | 96.2% | 86.1% |
| Comparative Example 9 | — | — | 99.2% | 95.2% |
| Comparative Example 10 | — | — | precipitation | precipitation |

Therefore, as for an anti-inflammatory analgesic pharmaceutical composition containing piroxicam or its pharmaceutically acceptable salt and hyaluronic acid or its pharmaceutically acceptable salt as active ingredients, a liquid composition containing β-cyclodextrin or its derivative and polyethylene glycol can provide a physicochemically stable liquid injection.

The invention claimed is:

1. An anti-inflammatory, analgesic pharmaceutical composition, consisting of (1) piroxicam or a pharmaceutically acceptable salt thereof and hyaluronic acid or a pharmaceutically acceptable salt thereof as active ingredients; (2) β-cyclodextrin or its derivative and polyethylene glycol as stabilizing agents; and (3) a pharmaceutically acceptable carrier for administration of the pharmaceutical composition by injection.

2. The composition according to claim 1 wherein the concentration of piroxicam or a pharmaceutically acceptable salt thereof and hyaluronic or a pharmaceutically acceptable salt thereof is between 0.5% and 10.0% by weight and 0.5% and 5.0% by weight, respectively.

3. The composition according to claim 2 wherein the concentration of piroxicam or a pharmaceutically acceptable salt thereof and hyaluronic or a pharmaceutically acceptable salt thereof is between 1.0% and 3.0% by weight and 1.0% and 3.0% by weight, respectively.

4. The composition according to claim 1 wherein β-cyclodextrin or its derivatives is selected from the group consisting of 2,6-dimethyl-β-cyclodextrin, 2-hydroxyethyl-β-cyclodextrin, 2-hydroxypropyl-β-cyclodextrin, (2-carboxymethoxy)propyl-β-cyclodextrin and sulfobutyl ether-7-β-cyclodextrin.

5. The composition according to claim 4, wherein β-cyclodextrin or its derivatives is 2-hydroxypropyl-β-cyclodextrin.

6. The composition according to claim 1, wherein the mean molecular weight of polyethylene glycol is between 200 and 100,000.

7. The composition according to claim 1, wherein an amount of the stabilizing agents is from 5 to 50 times of the weight of piroxicam or a pharmaceutically acceptable salt thereof.

8. The composition according to claim 7, wherein the amount of the stabilizing agents is from 10 to 45 times of the weight of piroxicam or a pharmaceutically acceptable salt thereof.

9. The composition according to claim 1, wherein the ratio between β-cyclodextrin and polyethylene glycol is 30:1 to 1:20.

10. The composition according to claim 9, wherein β-cyclodextrin and polyethylene glycol is 15:1 to 1:10.

11. The composition according to claim 1, wherein the pH of the composition is from 5.5 to 8.5.

12. The composition according to claim 11, wherein the pH of the composition is from 7.0 to 8.5.

13. A method of preparing a pharmaceutical composition consisting of:
   a) dissolving piroxicam or a pharmaceutically acceptable salt thereof with β-cyclodextrin and polyethylene glycol in a solvent thereby making a solution containing piroxicam;
   b) adding hyaluronic acid or a pharmaceutically acceptable salt thereof as well as a pharmaceutically acceptable carrier for administration of the pharmaceutical composition by injection to the solution containing piroxicam
   wherein said pharmaceutical composition is the pharmaceutical composition of claim 1.

14. The method according to claim 13, wherein the pharmaceutically acceptable salt of piroxicam is formed by adding salt into the piroxicam solution.

* * * * *